United States Patent
Polo (10) Patent No.: US 11,272,910 B1
(45) Date of Patent: Mar. 15, 2022

(54) CONTAINMENT SYSTEM FOR LAPAROSCOPIC MORCELLATION AND METHODS OF USE

(71) Applicant: Oscar Polo, Portland, OR (US)

(72) Inventor: Oscar Polo, Portland, OR (US)

(*) Notice: Subject to any disclaimer, the term of this patent is extended or adjusted under 35 U.S.C. 154(b) by 0 days.

(21) Appl. No.: 17/498,506

(22) Filed: Oct. 11, 2021

Related U.S. Application Data (63) Continuation of application No. 17/308,269, filed on May 5, 2021, now Pat. No. 11,191,529.

(51) Int. Cl.
*A61B 17/00* (2006.01)
*A61B 17/32* (2006.01)

(52) U.S. Cl.
CPC ........... *A61B 17/00234* (2013.01); *A61B 2017/00287* (2013.01); *A61B 2017/00862* (2013.01); *A61B 2017/320024* (2013.01)

(58) Field of Classification Search
CPC .......... A61B 17/00234; A61B 17/3423; A61B 17/221; A61B 2017/00287; A61B 2017/00862; A61B 2017/320024; A61B 2017/00557; A61B 2017/0225; A61B 90/40; A61B 10/02; A61B 1/313; A61B 1/3132; A61J 1/10; A61J 1/1412
See application file for complete search history.

(56) References Cited

U.S. PATENT DOCUMENTS

2018/0049771 A1* 2/2018 Rhemrev-Pieters ... A61B 90/40

* cited by examiner

*Primary Examiner* — Mohamed G Gabr
(74) *Attorney, Agent, or Firm* — Marc Baumgartner; Baumgartner Patent Law (57) ABSTRACT

A collapsible and expandable containment system for laparoscopic morcellation that can be inserted into a patient's cavity and configured for a targeted tissue specimen to be placed inside through a closable large opening. The containment system includes a thin, flexible membrane defining an internal cavity and having an opening for insertion of the biological specimen into the internal cavity. Said system can include one or more pouches having a proximal opening on the membrane and that extend towards the internal cavity, terminating at a distal segment. The one or more pouches are configured to allow passage of a laparoscopic instrument shaft into the internal cavity, such that the distal segment of the one or more pouches conforms to the instrument shaft. Additional embodiments are directed to containment systems having a retractable sleeve for removal of the morcellation specimen.

10 Claims, 11 Drawing Sheets

CONTAINMENT SYSTEM FOR LAPAROSCOPIC MORCELLATION AND METHODS OF USE

CROSS-REFERENCE TO RELATED APPLICATIONS

This application claims priority to, and is a continuation of, U.S. patent application Ser. No. 17/308,269, filed on May 5, 2021, which is incorporated herein by reference in its entirety.

FIELD OF THE INVENTION

The teachings herein relate to methods and compositions useful in laparoscopic power morcellation. More specifically, the embodiments herein relate to receptacles configured to prevent occult cancerous morcellated particulate tissue from spreading into areas inside the patient away from the cutting site.

BACKGROUND

Figure 5A:
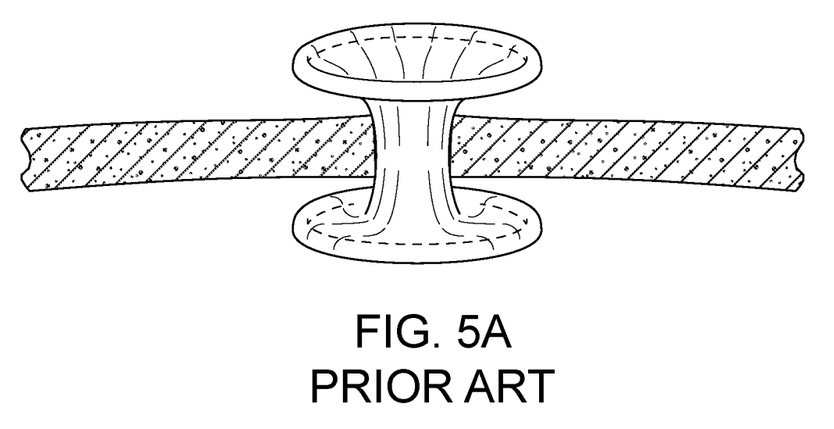
FIG. 5A is a perspective view a prior art flexible retractor.
Figure 5B:
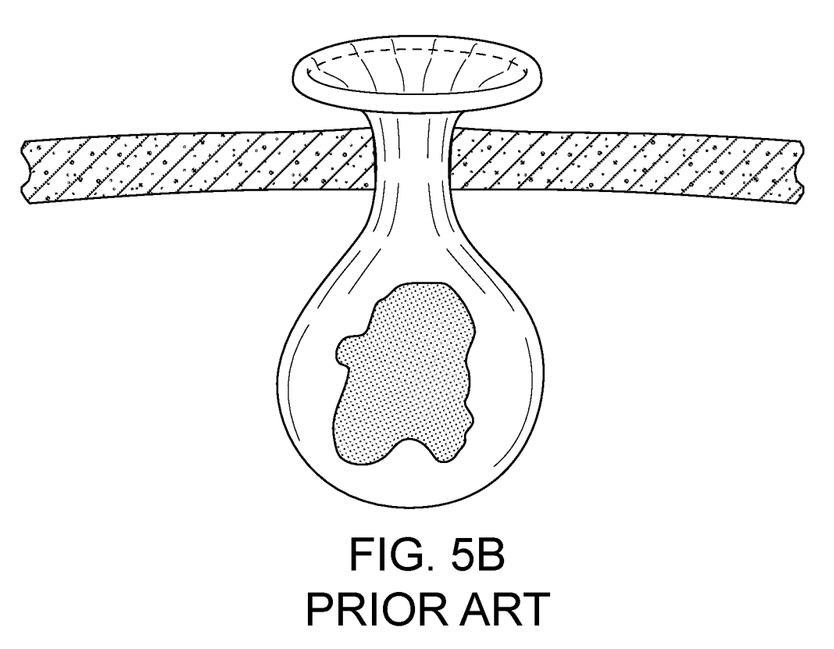
FIG. 5B is a perspective view of a prior art flexible bag.

Power morcellators are devices, used in laparoscopic surgery that morcellate, or cut tissue, into smaller pieces to allow for removal through small surgical access ports. Currently uncontained laparoscopic power morcellation for the removal of the uterus (hysterectomy) or uterine fibroids (myomectomy) is discouraged because, based on an analysis of currently available data, it may pose a risk of inadvertently spreading cancerous tissue, notably uterine sarcomas, beyond the uterus. In attempts to prevent the potential spread of cancerous tissue, morcellation containment systems have been designed with the goal of containing the specimen that is being cut and to remove the severed pieces as they are being cut. Current containment systems for laparoscopic surgery are used for receiving a specimen. One style of container currently being used is a bag-like container having a large proximal opening, having a flexible collar, and that is inserted into the abdominal cavity through a 3 to 5 cm incision. Once the bag is positioned inside the abdominal cavity, the tissue to be morcellated is inserted into the bag through the proximal opening. The collar of the opening is then pulled outside the patient through the incision to give access to a cutting device, such as a hand-held scalpel or power morcellator, and other surgical instruments such as a grasper and laparoscope. See for example, U.S. Patent Publication No. 2014/0236168 to Shibley. This style of prior art bag is shown in FIG. 5B. Unfortunately, containers like Shibley do not give the surgeon the room or visibility to perform power morcellation within them without unnecessarily increasing the size of the incision in the patient.

In attempts to improve the mobility and visibility to the surgeon using smaller incisions, newer containment systems were developed that have 1 or more secondary ports for the insertion of the laparoscopic instruments and/or removal of the morcellated specimen. To decrease contamination from the tissue being morcellated, the secondary ports for insertion of instruments are narrow flexible sleeves that are brought out of the abdominal cavity through trocar sleeves and are used for the insertion of the instruments. See for example, U.S. Patent Publication No. 2016/0338682 to Hoyte, shown herein as FIG. 5C. Adding these sleeves for the insertion of instruments, increases bulk, minimizing the ability to insert the containment system through a laparoscopic port, increases the number of surgical steps the surgeon must perform, decreases visibility, and increases the risk of contamination from the sleeve being reinserted into the cavity.

In another newer containment system, the opening for removal of morcellated tissue is a different opening than the insertion of the tissue to be morcellated. However, an embodiment of this design teaches a large caliber trocar sleeve is positioned inside the opening for removal of morcellated tissue and the tissue is removed through the trocar sleeve. See for example U.S. Pat. No. 10,337,139 to Polo. A limitation of this system is that the firm distal end of the trocar sleeve tends to catch the morcellated tissue as it is being removed, rendering an inefficiency. Furthermore, there is potential for a contamination on the outside of the trocar sleeve from the morcellated tissue, which increases a cancer exposure risk to the anterior cavity wall as the trocar sleeve is being removed from the cavity.

Accordingly, there is a need in the art for containment systems to be configured so that surgeons can have more visibility, and maneuverability for tissue morcellation: 1) without requiring larger incisions to be made for inserting the containment system into the abdominal cavity, 2) without multiple extraneous steps for the deployment of the containment system in preparation for tissue morcellation, 3) without increasing the risk of contamination to the cavity from tissue being removed through the opening for morcellated tissue, 4) without sacrificing maneuverability of the instruments, 5) without sacrificing visibility of the work space, and 6) without making it more difficult to remove the morcellated tissue from the patient's cavity.

The following disclosure describes expanding/collapsing receptacles configured for use with power morcellators that address this need in the art.

SUMMARY

Preferred embodiments are directed to a morcellation containment system used for laparoscopic morcellation comprising a thin, flexible membrane having an outer surface and an inner surface that defines an internal cavity sufficiently large enough to contain a biological specimen targeted for surgical morcellation within a patient, wherein the thin, flexible membrane comprises one or more pouches having a proximal opening on the membrane and extend 1 mm to 10 cm deep towards the internal cavity, terminating at a distal segment, wherein the one or more pouches are made of a thin, flexible material, and the proximal opening on the membrane is configured to allow passage of a laparoscopic instrument shaft having a diameter from 3 to 15 mm into the internal cavity, such that the distal segment of the one or more pouches conforms to the instrument shaft and wherein the containment system further comprises an opening on the outer surface of the membrane for insertion of the biological specimen into the internal cavity.

Preferred embodiments are directed to containment systems wherein the one or more pouches have an aperture in the distal segment that is positioned inside the internal cavity, and that conforms around the diameter of a laparoscopic instrument shaft when the laparoscopic instrument enters the internal cavity.

Preferred embodiments are directed to containment systems wherein the distal segment of the one or more pouches has an elastic aperture of a smaller or equal diameter to the shaft of the instrument passing through it.

Preferred embodiments are directed to containment systems wherein the distal segment of the one or more pouches lacks a premade aperture and is configured to be penetrated by an end of a laparoscopic instrument, such that the thin, flexible material conforms around the diameter of the laparoscopic instrument shaft after penetration.

Preferred embodiments are directed to containment systems wherein the one or more pouches is configured not to turn inside out, such that it does not protrude past the outer surface of the membrane and remains below the inner surface of the membrane.

Preferred embodiments are directed to containment systems wherein the one or more pouches is partially rotated into a swirling radial pattern shape.

Preferred embodiments are directed to containment systems further comprising one or more semirigid or rigid elements axially positioned within or externally coupled to the one or more pouches such that it extends from the proximal membrane opening to the distal segment of the pouch.

Preferred embodiments are directed to containment systems wherein the distal segment of one or more pouches is tethered to the inner surface of the membrane.

Preferred embodiments are directed to containment systems wherein there is a flexible ring of equal or larger outer diameter to the proximal opening is circumferentially coupled to the distal segment of the pouch.

Preferred embodiments are directed to containment systems further comprising one or more support ribbons positioned adjacent to the one or more pouches that is configured to be pulled away from the inner cavity to provide countertraction and help alignment when a laparoscopic instrument is positioned through the one or more pouches.

Preferred embodiments are directed to containment systems wherein the one or more support ribbons is configured in a loop.

Preferred embodiments are directed to containment systems wherein the outer surface of the membrane comprises one or more sheaths positioned adjacent to the one or more proximal pouch openings and are configured to contain and store the one or more support ribbons.

Preferred embodiments are directed to containment systems wherein the opening for insertion of the biological specimen is also configured to allow insertion of a morcellator instrument into the internal cavity.

Preferred embodiments are directed to containment systems used for laparoscopic morcellation comprising a thin, flexible membrane having an outer surface and an inner surface that defines an internal cavity sufficiently large enough to contain a biological specimen targeted for surgical morcellation within a patient, wherein the thin, flexible membrane comprises one or more pouches having a proximal opening on the membrane and extend 1mm to 10 cm deep towards the internal cavity, terminating at a distal segment, wherein the one or more pouches are made of a thin, flexible material, and the proximal opening on the membrane is configured to allow passage of a laparoscopic instrument shaft having a diameter from 3 to 15 mm into the internal cavity, such that the distal segment of the one or more pouches conforms to the instrument shaft and wherein the containment system further comprises an opening on the outer surface of the membrane for insertion of the biological specimen into the internal cavity, and further comprising an opening for removal of the morcellated biological specimen that is a smaller opening from the opening for insertion of the biological specimen, and is configured to allow the insertion and removal of the morcellator into the internal cavity.

Preferred embodiments are directed to containment systems further comprising a retractable sleeve of at least 3 cm in length, made of a thin flexible material, and comprising first and second openings, wherein the first opening of the sleeve encompasses, and is circumferentially coupled to the perimeter, or adjacent to said perimeter, of the opening for removal of the morcellated biological specimen.

Preferred embodiments are directed to containment systems further comprising a flexible ring 2 to 6 cm in diameter circumferentially coupled to the perimeter of the second opening of the sleeve and configured such that sleeve can be rolled up around it.

Preferred embodiments are directed to containment systems wherein the flexible ring is operably coupled to a pull cord for lengthening the sleeve away from the internal cavity.

Preferred embodiments are directed to methods of morcellating a biological specimen within a patient comprising: a) providing a containment system comprising a thin, flexible membrane having an outer surface and an inner surface that defines an internal cavity sufficiently large enough to contain a biological specimen targeted for surgical morcellation within a patient, wherein the thin, flexible membrane comprises one or more pouches having a proximal opening on the membrane and extend 1 mm to 10 cm deep towards the internal cavity, terminating at a distal segment, wherein the one or more pouches are made of a thin, flexible material, and the proximal opening on the membrane is configured to allow passage of a laparoscopic instrument with a shaft having a diameter from 3 to 15 mm into the internal cavity, such that the distal segment of the one or more pouches conforms to the instrument shaft and wherein the containment system further comprises an opening on the outer surface of the membrane for insertion of the biological specimen into the internal cavity; b) targeting a biological specimen for morcellation within a surgical cavity of a patient, wherein the surgical cavity comprises an anterior wall;

c) positioning the biological specimen into the internal cavity of the containment system through the opening for insertion of the biological specimen;

d) inserting one or more trocar sleeves into the surgical cavity such that they individually align with the proximal openings of the one or more pouches;

e) inserting one or more laparoscopic instruments through the one or more trocar sleeves, through the aligned one or more pouches, and into the internal cavity of the containment system, such that the distal segment of the one or more pouches conforms to the shaft of the one or more laparoscopic instruments;

f) inserting the morcellator through either the opening for insertion of the biological specimen or the one or more pouches and into the internal cavity; and g) morcellating the biological specimen with the morcellator such that no morcellated tissue escapes into the surgical cavity.

Preferred embodiments are directed to methods of morcellating a biological specimen within a patient comprising: a) providing a containment system comprising a thin, flexible membrane having an outer surface and an inner surface that defines an internal cavity sufficiently large enough to contain a biological specimen targeted for surgical morcellation within a patient, wherein the thin, flexible membrane comprises one or more opening on the membrane configured to allow passage of a laparoscopic instrument with a shaft having a diameter from 3 to 15 mm into the internal cavity, wherein the containment system further comprises an opening on the surface of the membrane for insertion of the biological specimen into the internal cavity; further comprising an opening for the removal of the morcellated biological specimen; and further comprising a retractable sleeve of at least 3 cm in length, made of a thin flexible material, and comprising first and second openings, wherein the first opening of the retractable sleeve encompasses, and is circumferentially coupled to the perimeter, or adjacent to said perimeter, of the opening for removal of the morcellated biological specimen, and wherein the second opening is circumferentially coupled to a flexible ring of 2 to 6 cm in diameter and configured such that the retractable sleeve can be rolled around said flexible ring. b) targeting a biological specimen for morcellation within a surgical cavity of a patient, wherein the surgical cavity comprises an anterior wall; c) positioning the biological specimen into the internal cavity of the containment system through the opening for insertion of the biological specimen and subsequently closing the opening; d) inserting one or more trocar sleeves into the surgical cavity such that they align with the proximal opening of the one or more pouches; e) inserting one or more laparoscopic instruments through the one or more trocar sleeves, through the aligned one or more pouches, and into the internal cavity such that the distal segment of the one or more pouches conforms to the shaft of the one or more laparoscopic instruments; f) inserting the morcellator into the internal cavity through an opening selected from the group consisting of: the opening for removal of the biological specimen, the one or more pouches, and the opening for insertion of the biological specimen; and g) morcellating the biological specimen with the morcellator such that no morcellated tissue escapes into the surgical cavity.

Preferred embodiments are directed to methods of morcellating a biological specimen within a patient comprising: a) providing a containment system comprising a thin, flexible membrane having an outer surface and an inner surface that defines an internal cavity sufficiently large enough to contain a biological specimen targeted for surgical morcellation within a patient, wherein the thin, flexible membrane comprises one or more opening on the membrane configured to allow passage of a laparoscopic instrument with a shaft having a diameter from 3 to 15 mm into the internal cavity, wherein the containment system further comprises an opening on the surface of the membrane for insertion of the biological specimen into the internal cavity; further comprising an opening for the removal of the morcellated biological specimen; and further comprising a retractable sleeve of at least 3 cm in length, made of a thin flexible material, and comprising first and second openings, wherein the first opening of the retractable sleeve encompasses, and is circumferentially coupled to the perimeter, or adjacent to said perimeter, of the opening for removal of the morcellated biological specimen, and wherein the second opening is circumferentially coupled to a flexible ring of 2 to 6 cm in diameter and configured such that the retractable sleeve can be rolled around said flexible ring; b) targeting a biological specimen for morcellation within a surgical cavity of a patient, wherein the surgical cavity comprises an anterior wall; c) positioning the biological specimen into the internal cavity of the containment system through the opening for insertion of the biological specimen and subsequently closing the opening; d) inserting one or more trocar sleeves into the surgical cavity such that they align with the proximal opening of the one or more pouches; e) inserting one or more laparoscopic instruments through the one or more trocar sleeves, through the aligned one or more pouches, and into the internal cavity such that the distal segment of the one or more pouches conforms to the shaft of the one or more laparoscopic instruments; f) inserting the morcellator into the internal cavity through an opening selected from the group consisting of: the opening for removal of the biological specimen, the one or more pouches, and the opening for insertion of the biological specimen; and g) morcellating the biological specimen with the morcellator such that no morcellated tissue escapes into the surgical cavity.

Preferred embodiments are directed to methods of morcellating a biological specimen wherein the morcellator is inserted and removed from the internal cavity through the retractable sleeve and the opening for removal of the biological specimen and morcellator.

Preferred embodiments are directed to methods of morcellating a biological specimen wherein the morcellator is inserted and removed from the internal cavity through a trocar sleeve that is positioned inside the retractable sleeve and extends into the internal cavity.

Preferred embodiments are directed to methods of morcellating a biological specimen wherein the containment system further comprises a pull string coupled to the flexible ring, and further comprising pulling the pull string such that the coupled flexible ring compresses and is pulled into the morcellator's trocar sleeve, and then removing the morcellator trocar sleeve from within the patient's anterior wall, thereby exteriorizing the retractable sleeve and flexible ring.

Preferred embodiments are directed to methods of morcellating a biological specimen further comprising rolling up the retractable sleeve around the exteriorized flexible ring.

Preferred embodiments are directed to methods of morcellating a biological specimen further comprising reinserting the morcellator trocar sleeve through the rolled up retractable sleeve and the opening for removal of biological specimen and inserting the morcellator through the morcellator trocar sleeve and into the internal cavity of the containment system.

BRIEF DESCRIPTION OF THE DRAWINGS

It will be appreciated that the drawings are not necessarily to scale, with emphasis instead being placed on illustrating the various aspects and features embodiments of the invention, in which.

DETAILED DESCRIPTION OF THE ILLUSTRATED EMBODIMENTS

Embodiments of the present invention are described below. It is, however, expressly noted that the present invention is not limited to these embodiments, but rather the intention is that modifications that are apparent to the person skilled in the art and equivalents thereof are also included.

FIGS. 1, 2, 3, and 9 show the collapsible containment system 2 in an expanded position. According to preferred embodiments, the containment system 2 has a thin, flexible membrane 16 that surrounds and defines an enclosed internal cavity 26. The membrane 16 is preferably impermeable to gases and fluids, to prevent leakage if the containment system 2 is being insufflated.

According to preferred embodiments, the containment system 2 comprises one or more pouches 20, made of the same or different material than the membrane 16, each having a proximal opening 18 on the membrane 16 and extend 1 mm to 10 cm deep towards the internal cavity, 26 terminating at a distal segment 22. The one or more pouches 20 preferably have a conical shape with a circular proximal opening 18, or otherwise taper towards their distal section 22. According to preferred embodiments, the pouches extend about 0.5-2.5 cm, e.g., 1 cm, in length away from the internal face of the membrane 16 in a conical shape with the proximal opening 18 being about 10-20 mm, such as 15 mm, in diameter and the tip at its distal end narrows to about 5 mm diameter, or substantially the same diameter as the shaft of the selected instrument. The taper of the pouch 20 is advantageous as the wider proximal opening 18 allows for easier insertion of the laparoscopic instrument (e.g., a laparoscope 38 or grasper 30) and the narrowing helps the pouch 20, including its distal section 22, conform to the perimeter of the shaft of the laparoscopic instrument (e.g., 30 and 38) to help mitigate or stop particulate spread outside the containment system 2. While shown as circular, according to further embodiments, the proximal opening can be shaped in any suitable configuration, non-exclusively including polygonal shapes (e.g., square, rectangle, triangle, pentagon, hexagon, octagon), cross or star-shaped. Similarly, while shown as conical, the pouches themselves can be any suitable shape, including cubes, rectangle prism, pyramids, pentagon prism, hexagon prism, and octagon prism, although it is preferred that the pouch tapers from the proximal opening 18 to the distal section 22.

Preferably, the one or more pouches 20 are made of a thin, flexible, and elastic material, such as polyurethane, and the proximal opening 18 on the membrane is configured to allow passage of a laparoscopic instrument (e.g., a laparoscope 38 or grasper 30) shaft having a diameter from 3 to 15 mm into the internal cavity 26, such that the distal segment 22 of the one or more pouches 20 conforms to the instrument shaft. This conformity or elastic grip between the distal segment 22 to the instrument (e.g., laparoscope 38 or grasper 30) helps prevent specimen 40 particulate from escaping the internal cavity 26 during morcellation. Pouches 20 that extend internally towards the internal cavity 26 eliminate the need to have longer container sleeves that extend away from the container with the proximal ends externalized through a second incision, so that the trocar sleeve can then be reinserted through the container sleeve. See for example, U.S. Patent Publication No. 2016/0338682 to Hoyte. As known in the art, the laparoscope 38 allows the practitioner to view the internal cavity 26 and the specimen 40, while the grasper 30 allows the practitioner to hold and manipulate the specimen 40 whether before, during, or after morcellation.

Figure 2:
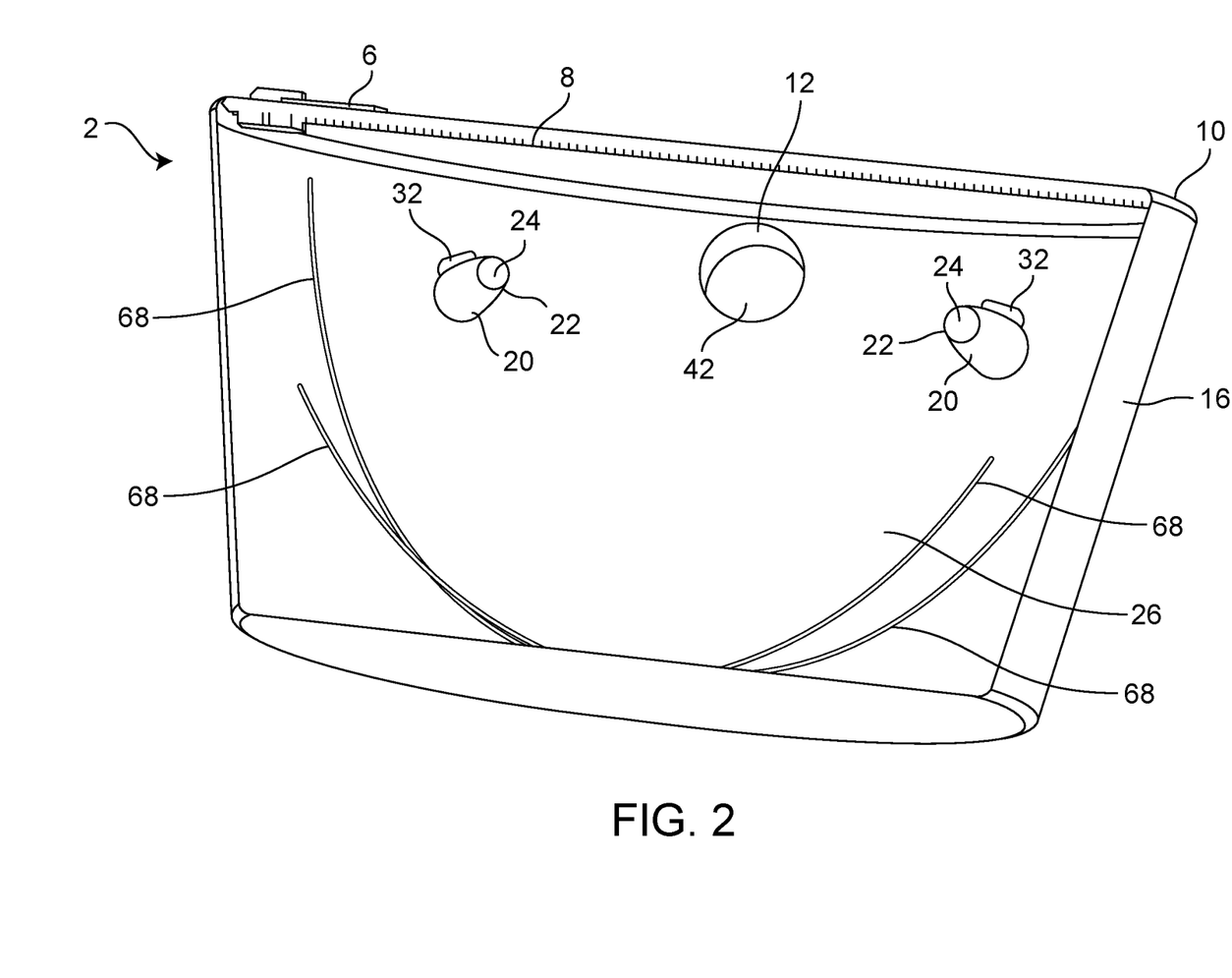
FIG. 2 is a perspective cross-sectional view of the internal cavity of an expanded containment system showing pouches with support rods.
Figure 3:
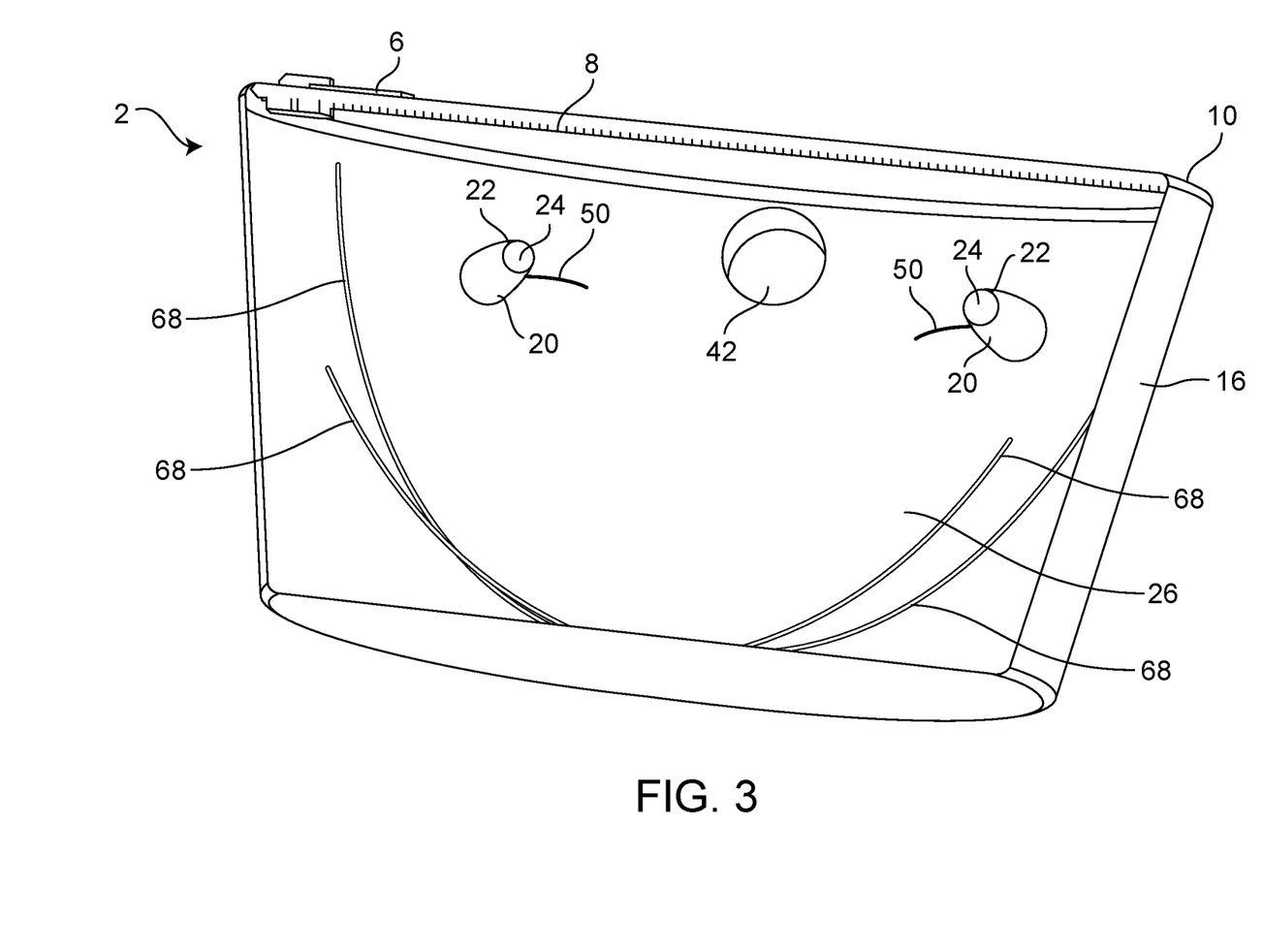
FIG. 3 is a perspective cross-sectional view of the internal cavity of an expanded containment system showing pouches with tethers.
Figure 10:
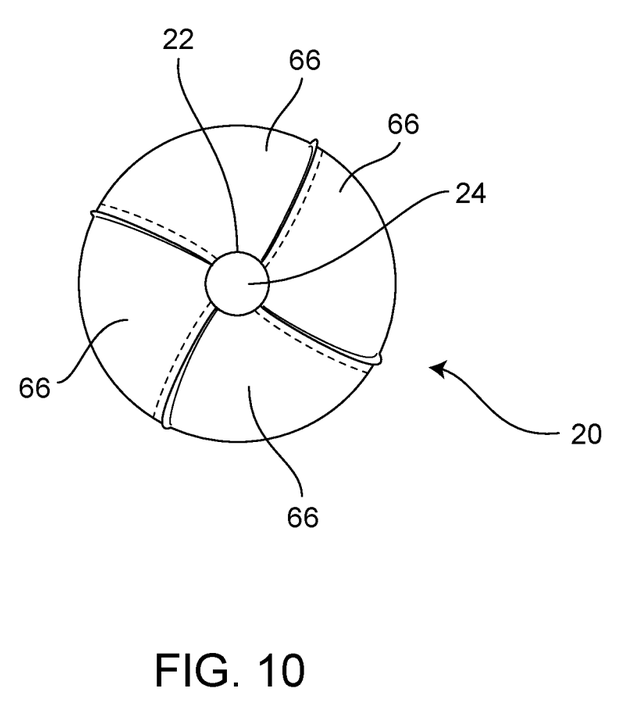
FIG. 10 is a closeup bottom view of a pouch made up of a plurality of axially aligned flaps.

It is preferred that pouches 20 are configured such that they don't turn inside out, such that they are pulled outside of the internal cavity 26 when a laparoscopic instrument (e.g., 30 and 38) is removed from the pouch. This is advantageous as it helps prevent potential specimen particulate from the inside of the internal cavity 26 or otherwise located within the pouch 20 from spreading outside the containment system 2. As shown, each pouch can have one rod 32 axially positioned per pouch 20. Alternatively, each pouch can have a plurality of axially positioned rods, spaced apart to prevent the pouch from everting. FIGS. 2 and 3 show two non-exclusive ways of preventing the pouches 20 from inverting to the outside of the containment system 2. Specifically, FIG. 2 shows pouch rods 32 that are axially coupled to both the pouch 20 and the internal face of the membrane 16 within the internal cavity 26. These pouch rods 26 can be made of a rigid, or semi-rigid material, such as metal or plastic. According to preferred embodiments, the pouch support rods 32 can act as a hinge such that the pouch 20 folds against the internal face of the membrane to effectively close the pouch's proximal opening 18 as the laparoscopic instrument (e.g., 30 and 38) is removed from the containment system 2. FIG. 3 shows a pouch 20 that is prevented from eversion through the use of a tether 50 (e.g., thin cord or wire) that is coupled to both the pouch 20 (preferably the distal section 22) and the internal face of the membrane. Another alternative would be to make the pouch of a semirigid material that will not evert with upward traction of the distal end of the pouch. The pouch can be made of one solid piece or from a plurality of axially aligned flaps 66 that are adjacent to or partially overlapping, such as shown in FIG. 10. According to preferred embodiments, the pouch should have a low or limited profile at the proximal opening 18 on the outer membrane so as to allow the container to fit through the laparoscopic opening.

Figure 8A:
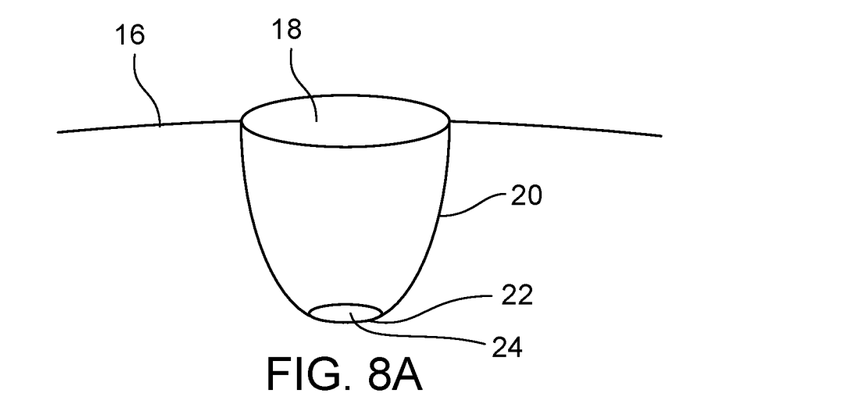
FIG. 8A is a closeup view of a pouch having a distal opening on its distal section.
Figure 8B:
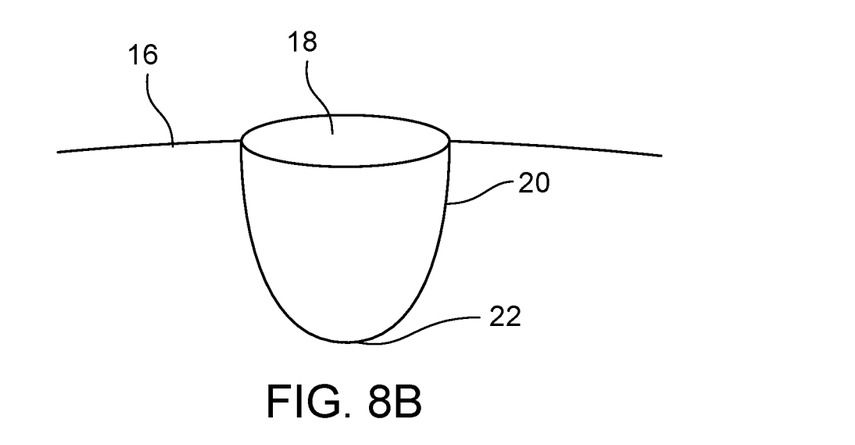
FIG. 8B is a closeup view of a pouch having a closed distal section, configured to be penetrable by a surgical instrument.

FIGS. 8A and 8B show two non-exclusive examples of pouches 20 that can be used with the teachings herein. FIG. 8A is a closeup view of a pouch 20 having a distal opening 24 on its distal section 22. Under this embodiment, when a laparoscopic instrument (e.g., 30 and 38) is inserted into the internal cavity 26 through the pouch 20, the perimeter of the distal opening 24 conforms to the shaft of the laparoscopic instrument (e.g., 30 and 38). This can be done multiple ways, non-exclusively including the utilization of an elastic perimeter for the distal opening 24. The elastic perimeter can have a smaller perimeter than the shaft of the laparoscopic instrument (e.g., 30 and 38), thus, when the laparoscopic instrument (e.g., 30 and 38) passes through the distal opening 24 it can expand its perimeter and creates a somewhat tight fit around the instrument. Alternatively, the perimeter of the distal opening 24 can be non-elastic and just be slightly bigger than the shaft of the laparoscopic instrument (e.g., 30 and 38), such that it still fits snug around the instrument to prevent particulate spread or the escape of insufflating gas. Alternatively, FIG. 8B is a closeup view of a pouch 20 having a closed distal section 22, configured to be penetrable by the working end of a laparoscopic instrument (e.g., 30 and 38), which could be a laparoscope, grasper, or morcellator. The distal section 22 preferably fits snugly (or has a small gap) around the shaft of the laparoscopic instrument (e.g., 30 and 38) after penetration, to mitigate particulate spread or the escape of insufflating gas. This can be done by having the distal section 22 or preferably the entire pouch 20 being made of a penetrable elastic material. While shown as circular, according to further embodiments, the distal opening 24 can be shaped in any suitable configuration, non-exclusively including polygonal shapes (e.g., square, rectangle, triangle, pentagon, hexagon, octagon) and star and cross shaped. According to certain embodiments the distal opening 24 can be a slit, for example.

While the pouches 20 are preferably configured for insertion/removal of non-morcellator laparoscopic instruments, such as a laparoscope 38 or grasper 30, according to non-preferred embodiments, a morcellator 28 can be inserted/removed through a pouch 20 instead of a retractable sleeve 12. Under these embodiments, a third pouch can be positioned at the opening 42 for removal of biological specimen, or elsewhere on the membrane 16 to allow insertion of the morcellator 28. Accordingly, all embodiments directed to the interaction between laparoscopic instruments and pouches can also expressly encompass embodiments wherein the morcellator 28 is a laparoscopic instrument.

Preferably the containment system 2 is collapsible/expandible such that it can be sized to fit within and through an opening between 14-20 mm in width but not when expanded in a natural open position. To facilitate the collapsing and expanding, the containment system 2 can include a plurality (e.g., 2, 3, 4 or more) of support rods 68 positioned in a circumferential and are radially spaced apart (whether equidistant or not from each other) around an axis, or substantially so, and having proximal ends extending proximally and laterally away from a base and configured such that the support rods 68 can move towards each other when the containment system 2 is collapsing and move away from each other when the containment system 2 is opening. The membrane 16 that is preferably water resistant, low-friction, tear-resistant, and made of material different from the support rods 68, and having a thickness between 0.05-0.15 mm, can be positioned (e.g., wrapped) along the support rods 68. Non-limiting examples of support rods 68 that can be used with the present invention are found in U.S. Pat. No. 10,478,166, which is hereby incorporated by reference in its entirety.

Figure 1:
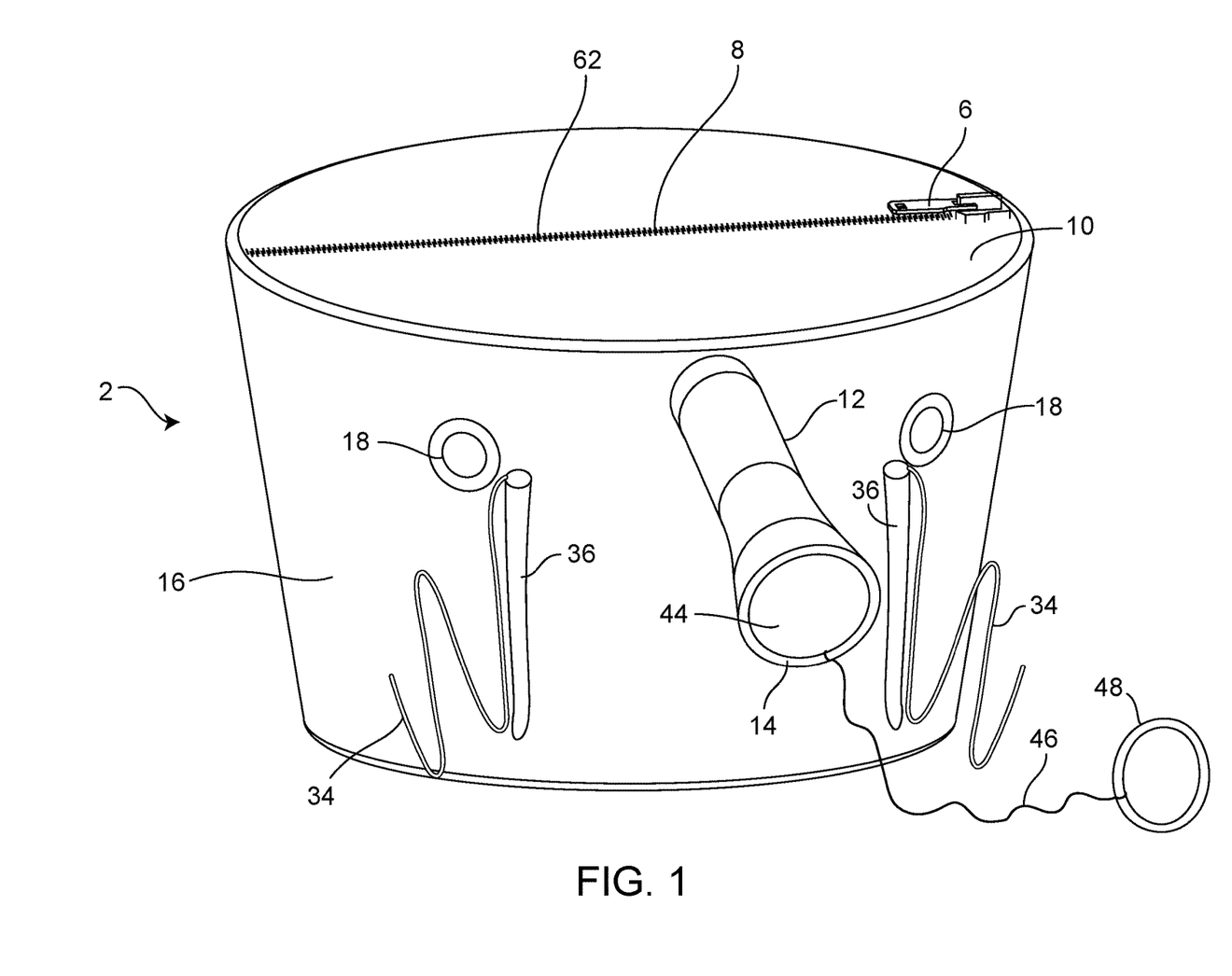
FIG. 1 is a perspective view of an expanded containment system with the retractable sleeve positioned externally to the containment system in an extended position.
Figure 4:
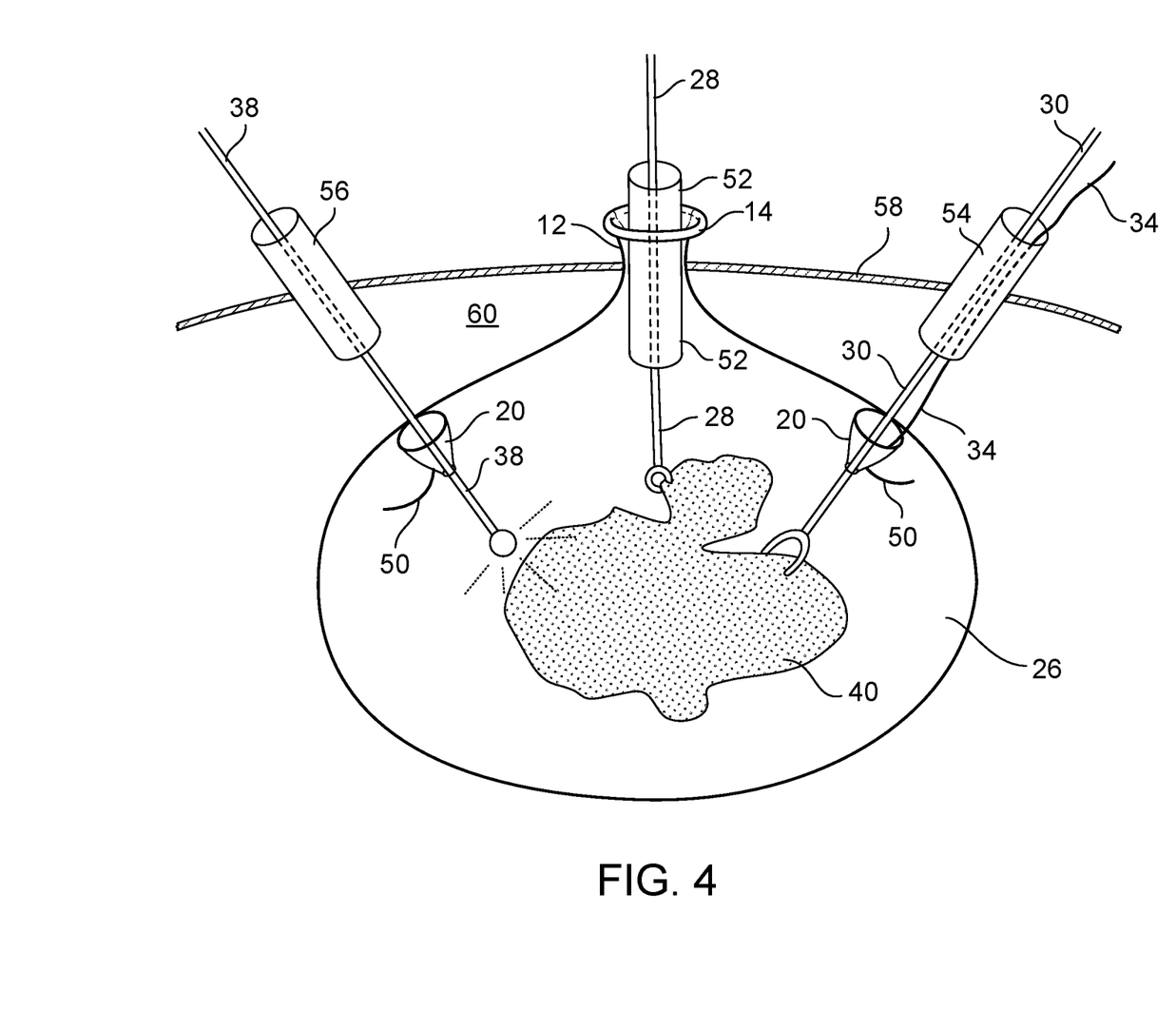
FIG. 4. is a perspective cross-sectional view of the internal cavity of an expanded containment system showing the morcellator, laparoscope, and grasper interacting with a biological specimen.
Figure 7:
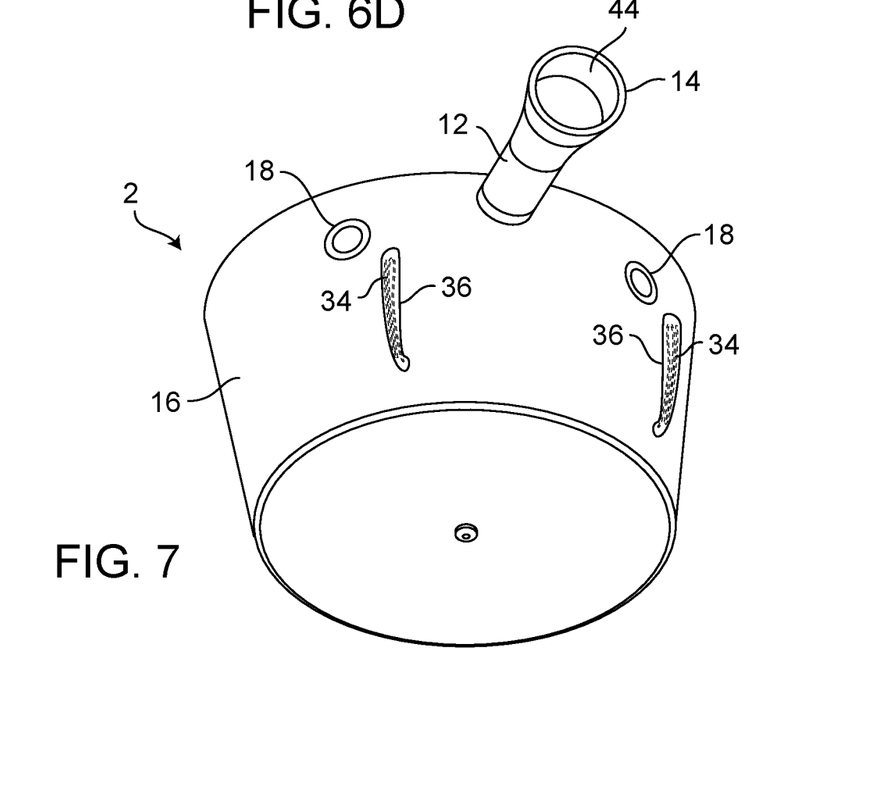
FIG. 7 is a perspective view of an expanded receptacle with the ribbons positioned inside the ribbon sheaths.

To help facilitate the insertion of laparoscopic instruments (e.g., 30 and 38) into the pouches 20, ribbons 34 can be coupled to the external membrane 16 adjacent to or abutting the proximal openings 18 of the pouch 20. As shown in FIG. 4, the ribbons 34 are externally pulled away from the patient to create tautness, preferably passed through their respective trocar sleeves 56 and 54 or alternatively, adjacent to the sheath 36. This tautness provides countertraction to help alignment when a laparoscopic instrument (e.g., 30 and 38) is positioned through the one or more pouches 20. These ribbons 34 can be configured as a continuous loop, and can thus be cut after the laparoscopic instruments (e.g., 30 and 38) are passed through the pouches 20 or just prior to removal of the containment system. Advantageously, and as shown in FIG. 1, the external surface of the membrane 16 includes one or more sheaths 36 positioned adjacent to and configured to store the ribbons 34 prior to pulling them for insertion of the instruments (e.g., 30 and 38) into their respective pouches 20. FIG. 7 shows the ribbons 24 stored within their respective sheaths 36. According to preferred embodiments, the ribbons 34 are positioned in their sheaths 36 at the time of insertion of the containment system 2 into the patient's cavity 60. The ribbons 34 are pulled through their respective trocar sleeves (e.g., 54 and 56) prior to insertion of the specimen 40 into the containment system 2. The instruments (e.g., 30 and 38) are then preferably passed through their respective trocar sleeves (e.g., 54 and 56) and through their respective pouches 20. According to certain embodiments, the ribbons 34 are individually configured as a loop. According to further embodiments, other elements that can be pulled, including tabs, can be positioned adjacent to or abutting the proximal openings 18 and used to provide tautness and countertraction to help alignment when a laparoscopic instrument is inserted. These tabs can be accessed through the use of grasping instruments inserted through the trocar sleeves.

The containment system 2 further comprises an opening 62 on the outer surface of the membrane 16 for insertion of the biological specimen 40 into the internal cavity 26. Preferably the opening 62 is a large closable opening positioned on a cover 10, or other surface area of the membrane 16, and is configured for insertion of a biological specimen 40 targeted for morcellation. The cover 10 is preferably made of the same material as the rest of the membrane 16, or is otherwise made of a thin, flexible, fluid impermeable material.

As one example, the closable opening 62 can be open and closed using any suitable components, including hook and loop fasteners, flaps, sliding tabs, but preferably uses a zipper 8. Non-exclusive examples of opening and closing the specimen opening 62 can be found in U.S. Pat. No. 10,478,166 to Polo (which is hereby incorporate by reference in its entirety) and preferably include a first track of zipper teeth that runs parallel to and are engaged to a complementary second track of zipper teeth thereby closing the central opening 62. A zipper slider 6 can be operably coupled to both first and second tracks that is configured to open and close the zipper 8 by moving in a first and opposite direction respectively. Under this embodiment, the central opening 62 can be completely closed, which is advantageous to mitigate or stop spreading specimen particulate during morcellation. According to certain embodiments, the zipper slider 6 has a loop or tab extending from it that can be grabbed by a grasper or instrument to making opening and closing easier for the practitioner.

Figure 9:
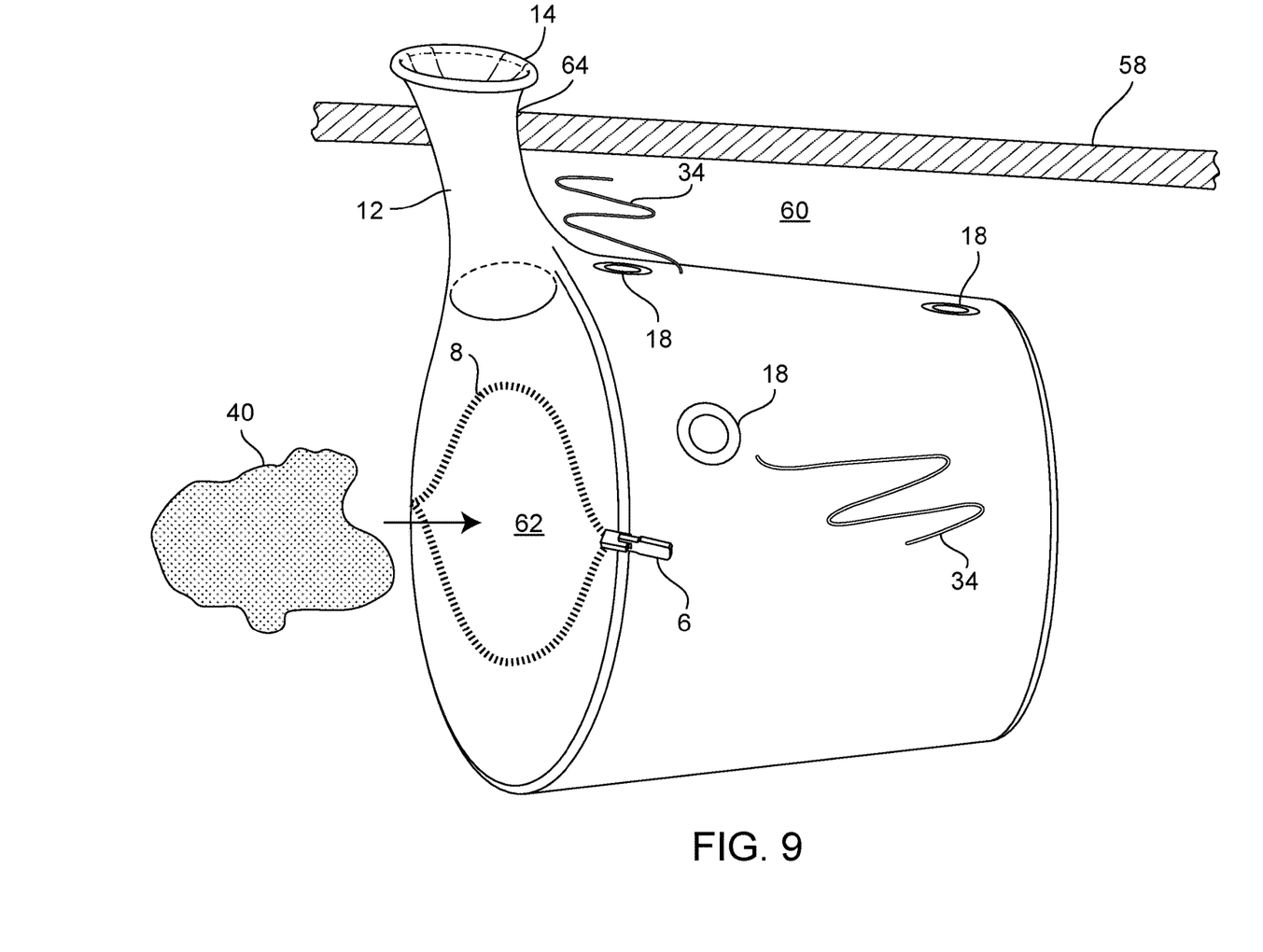
FIG. 9 is a perspective view of a specimen being inserted into the specimen opening of the containment system.

The large specimen opening 62 is preferably positioned on a cover 10 or other surface area of the containment system 2, such as the side. According to other embodiments, the retractable sleeve 12 and/or the proximal openings 18 for the pouches 20 can be positioned on the same surface (e.g., cover 10 or side) as the specimen opening 62 or the retractable sleeve can be positioned on the cover 10 with the large specimen opening 62 and the proximal openings 18 of the pouches 20 can be positioned on the side of the containment system 2, such as shown in FIG. 9. Alternatively, and as shown in FIG. 1 the retractable sleeve 12 and/or the proximal openings 18 for the pouches 20 can be positioned on the same side surface, different from the cover 10 where the large specimen opening 62 is positioned. It is also possible to have the opening for biological specimen be on the perimeter of the cover and side of the container, giving the opening a curvilinear shape.

In addition to the opening 62 for insertion of the biological specimen 40, it is preferred that the membrane 16 of the containment system 2 includes a separate opening 42 for the removal of morcellated specimen. The removal opening 42 is shown in FIGS. 2 and 3 and is positioned on the opposite end of the ring opening 44 of the retractable sleeve 12 defined by ring 14, for embodiments where a retractable sleeve 12 is used. Preferably, the opening 42 for removal of the morcellated specimen and retractable sleeve 12 are also configured to be used for the insertion and removal of a power morcellator 28, whether through the use of a morcellator trocar sleeve 52.

Figure 5C:
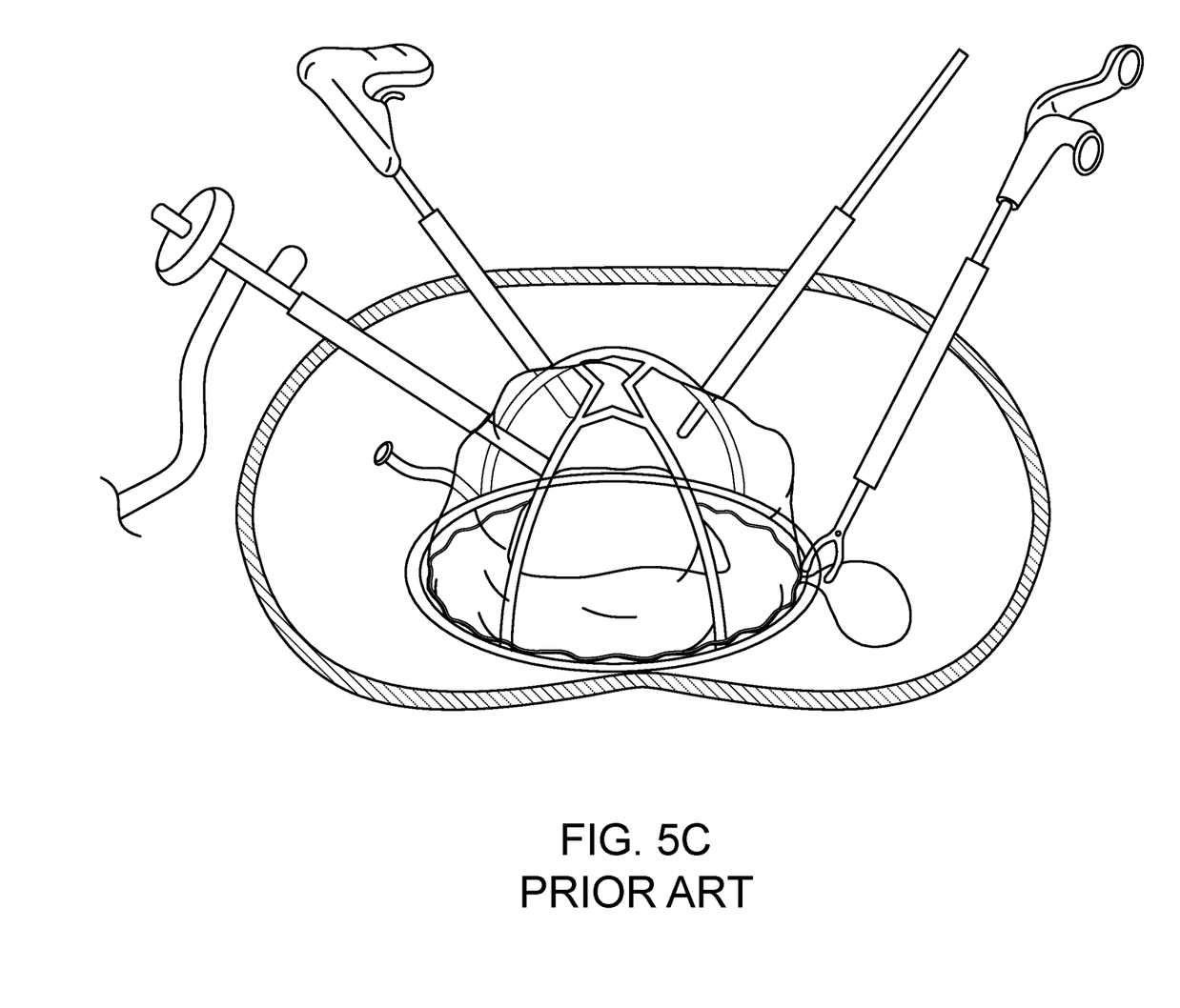
FIG. 5C is a perspective view of a prior art bag having extracorporeal sleeves instead of pouches.
Figure 6A:
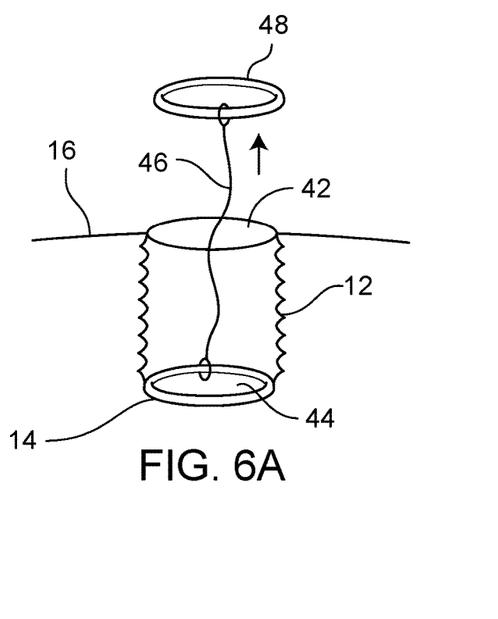
FIG. 6A is a perspective view of the retractable sleeve positioned within the internal cavity of the containment system.

In the preferred embodiment the opening 42 for removal of morcellated tissue is smaller than the opening 62 for the insertion of tissue and is circumferentially coupled to a first end of a flexible, retractable sleeve 12. The retractable sleeve 12 is made of a thin, flexible material, such as polyurethane, and is preferably of greater than or equal to 2.5 cm long when extended (as opposed to rolled up) and has a flexible ring 14 circumferentially coupled to its second end, positioned farther away from the membrane 16. The ring 14 is flexible, such as made of latex or rubber so that it can be compressed from its natural expanded configuration. The ring 14 is preferably coupled to a pull string 46 which in turn is coupled to a pull ring 48 or other member configured for grasping and pulling. According to preferred methods, if present, the retractable sleeve 12 is the only flexible sleeve coupled to the containment system 2, such that the containment system 2 lacks a plurality of attached flexible sleeves that are configured to have openings positioned outside the patient's internal cavity 60 for insertion of instruments within, such as shown in prior art system like FIG. 5C. While preferred containment systems have both one or more pouches 20 and a retractable sleeve 12, non-preferred embodiments embody containment systems 2 provided herein can, a) have pouches and lack a retractable sleeve, or b) lack pouches and only have a retractable sleeve 12, The following is a preferred embodiment of using the containment systems 2 herein. For insertion of the containment system 2, an incision 64 is made into the anterior wall 58 (e.g., abdominal wall), to provide access to the surgical cavity 60 where the targeted specimen 40 is located. A trocar sleeve 52, preferably between 10-20 mm in diameter, e.g., 15 mm, is positioned through the incision 64 into the cavity 60. The containment system 2 is in a collapsed configuration for insertion with the retractable sleeve 12 positioned inside the internal cavity 26 of the containment system 2. However it is preferred that the the connected pull ring 48 remains outside the cavity 60 and the trocar 52 during insertion, as discussed below. This configuration is shown in FIG. 6A.

The containment system 2 is positioned into the abdominal cavity and expands. As shown in FIG. 9, when deployed inside the patient in its expanded position, such as inside the abdominal cavity 60, the containment system 20 is preferably on its side with the opening 62 for insertion of tissue 40 into the internal cavity 26.

Figure 6B:
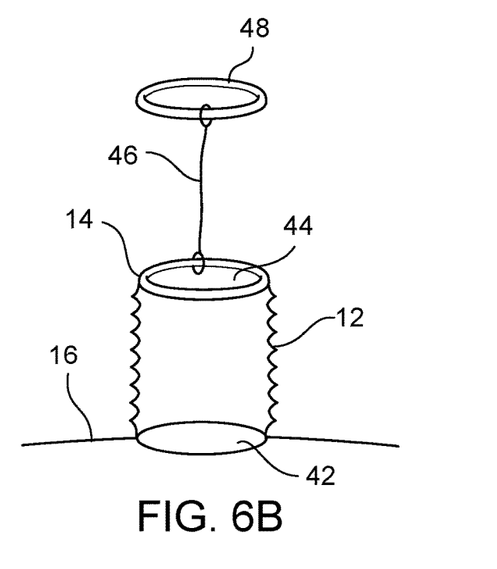
FIG. 6B is a perspective view of the retractable sleeve positioned externally to the containment system in an extended position.
Figure 6C:
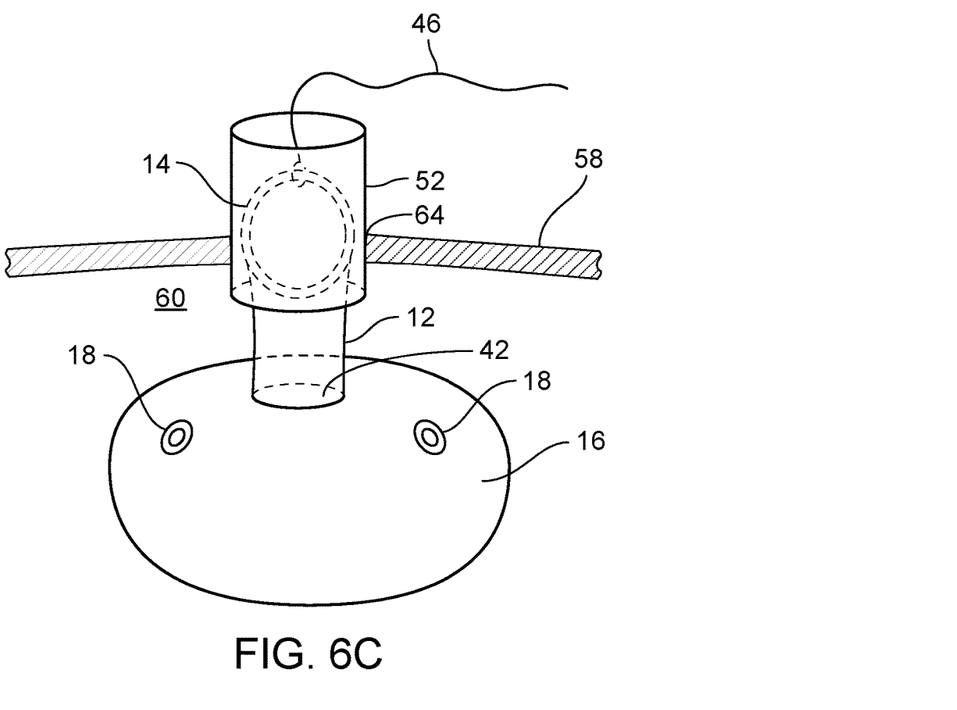
FIG. 6C is a perspective view of the containment system in an expanded positioned inside the patient with the retractable sleeve positioned externally to the containment system in an extended position within a trocar sleeve.
Figure 6D:
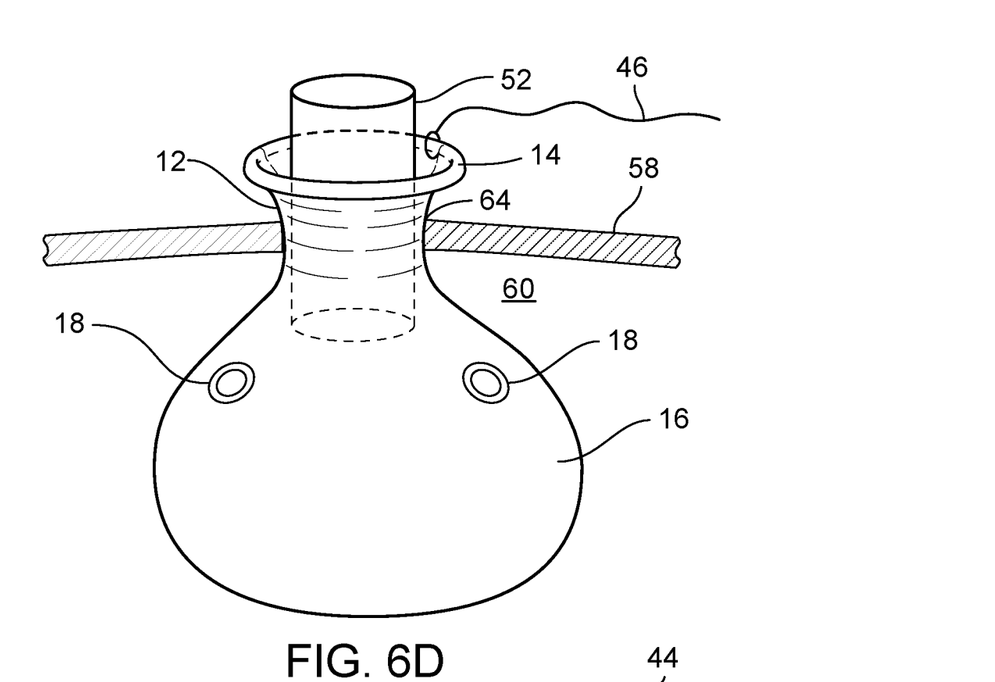
FIG. 6D is a perspective view of the containment system positioned inside the patient with the retractable sleeve rolled up around the ring.

After the specimen 40 is positioned inside the internal cavity 26 of the containment system 2, the opening 62 for insertion of specimen is zipped shut or otherwise closed depending on if using flaps or other types of closing mechanisms. The pull ring 48 or other pulling tab/member is then pulled away from the containment system 2 thereby everting and expanding the retractable sleeve 12 with its ring 14 leading the way through the opening 42 for removal of morcellated tissue and then into the trocar sleeve 52. This configuration is shown in FIG. 6C, while FIG. 6B shows the basic eversion of the retractable sleeve 12. In FIG. 6A, the ring 14 is positioned within the internal cavity 26 of the containment system 2, while in FIG. 6B, the ring 14 of the retractable sleeve 12 is now positioned outside the internal cavity 26 of the containment system 2. In FIG. 6C, the flexible ring 14 is compressed within the trocar sleeve 52. After the step shown in FIG. 6C, the trocar sleeve 52, with ring 14 positioned inside, is pulled out from the patient's anterior cavity wall 58 and the ring 14 and trocar sleeve 52 are separated leaving the ring 14 outside the anterior cavity wall 58. The retractable sleeve 12 is then rolled up around the ring 14 to reduce its length, and essentially approximating the opening 42 for removal of morcellated tissue to the opening 64 of the anterior cavity. As shown in FIG. 6D, the trocar sleeve 52 is then inserted through the rolled up retractable sleeve 12 back into the internal cavity 26 of the containment system 2. Preferably the trocar sleeve 52 includes a valve coupled to a gas source, whether a gas canister or the ambient air, and is used to inflate the bag. The morcellator 28 is then preferably inserted through the trocar sleeve 52 into the internal cavity 26 of the containment system 2 in order to morcellate the targeted specimen 40.

Preferably, the proximal end or cover 10 faces cephalad to the patient and the top side of the membrane faces towards the patient's anterior cavity wall 58 (e.g., abdominal wall). The opening for the removal of morcellated tissue 42 is preferably horizontally centrally located on the proximal, anterior top segment of the containment system 2, either on the cover 10 or on the side of the containment system 2, and is aligned with a larger trocar sleeve 52 (e.g., 15 mm trocar sleeve) in the patient's anterior cavity wall 58 (e.g., abdominal wall 58). The two proximal openings 18 of the pouches 20 are also preferably anteriorly located on the containment system 2, such as on either side of, and lateral to, the opening 42 for removal of morcellated tissue and retractable sleeve 12 (for embodiments where a retractable sleeve are used) and are aligned with their trocar sleeves 54 and 56 positioned through incisions the anterior wall 60. According to preferred embodiments, the trocar sleeves (e.g., 54 and 56) for the laparoscopic instruments are only aligned above the proximal openings 18 of the of the pouches 20 and are not intended to be inserted into the pouches, thereby reducing the risk of contamination to the anterior cavity wall from the outside distal segment of the trocar sleeve as they are being removed from the cavity. This is in contrast to prior art systems, such as shown in FIG. 5C, or U.S. Pat. No. 10,478,166 to Polo, where the trocar sleeves are positioned into the internal cavity of the bag.

With deployment of the containment system the ring 14 is positioned externally to the anterior wall of the cavity 58. The retractable sleeve 12 is preferably configured to be rolled around the ring 14 reducing the sleeve length, and essentially approximating the opening 42 for removal of morcellated tissue to the opening 64 of the anterior cavity. As shown in FIG. 4, the morcellator 28 is preferably positioned inside a suitably sized trocar sleeve 52 that is positioned inside the retractable sleeve 12 to allow its access into the internal cavity 26 of the containment system 2. According to other embodiments, the morcellator 28 can be passed into the internal cavity 26 of the containment system 2 through the retractable sleeve 12 without the use of a trocar sleeve. According to non-preferred embodiments, the morcellator 28 is inserted into the internal cavity 26 of the containment system 2 through either the opening 62 for insertion of the biological specimen or the one or more pouches 20, by using a trocar or not. For embodiments wherein the morcellator 28 is inserted through the opening 62 for insertion of the biological specimen it is preferred that the opening 62 is otherwise closed around or conforms to the morcellator (or trocar) so that specimen particulate cannot escape.

After morcellation, removal of the morcellated tissue 40 is preferably done directly through the flexible retractable sleeve 12 rather than through the morcellator's trocar sleeve 52 positioned inside the opening. Accordingly, for embodiments where a morcellator trocar sleeve 52 is used during morcellation, the morcellator 28 and then its trocar sleeve 52 are removed from within the retractable sleeve 12 before removing the morcellated specimen through the opening 42 for removal of the specimen and the retractable sleeve 12, and out the ring opening 44 positioned externally of the cavity wall 58 of the patient. After removal of the trocar sleeve 12 the containment system 2 is preferably configured to self-deflate after this step. The morcellated tissue pieces are then preferably removed through the rolled up retractable sleeve 12. Once the pieces are removed the retractable sleeve 12 is pulled and the entire containment system 2 is removed through the same incision 64 on the anterior cavity wall 58. The rolled-up segment of the retractable sleeve 12 can then grabbed by the practitioner either manually or with an instrument and with gentle anterior traction the entire containment system 2 slides through the same anterior cavity opening 64.

Collapsing and expanding the containment systems 2 herein allow for insertion and removal from the patient. Any suitable framework that provides structure and allows the containment system to be collapsed and expanded can be used in the teachings herein. As a non-exclusive example the support rods disclosed in U.S. Pat. No. 10,337,139 to Polo can be used with the teachings herein. This reference is expressly incorporated by reference in its entirety. More specifically, a plurality of at least two or three support rods positioned in a circumferential and equidistant manner around the vertical axis, or substantially so, and having proximal ends extending proximally and laterally away from the distal area and configured such that the support rods can move towards each other on the horizontal axis when the receptacle is collapsing and move away from each other on the horizontal axis when the receptacle is opening, The membrane herein can be a flexible liner that is water resistant, low-friction, tear-resistant, and made of material different from the support rods, having a thickness between 0.05-0.15 mm, wrapped along the support rods such as to define a containment system. All materials disclosed in U.S. Pat. No. 10,337,139, can also be used herein where suitable.

With respect to the large opening for specimen insertion 62, the disclosure of U.S. Pat. No. 10,337,139 is also applicable. Preferably, 62 is positioned centrally, or substantially so on the cover 10. The opening 62 can be configured to be entirely closed or substantially so, such that at least 75% of the opening is closed. More specifically, the edges of the opening 62 can be approximated so that they are adjacent to or overlapping each other resulting in over 75% occlusion or closure.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

The invention claimed is:

1. A containment system used for laparoscopic morcellation comprising a thin, flexible membrane having an outer surface and an inner surface that defines an internal cavity sufficiently large enough to contain a biological specimen targeted for surgical morcellation within a patient, and wherein the containment system further comprises a closable opening on the outer surface of the membrane for insertion of the biological specimen into the internal cavity, and further comprising an opening for removal of the morcellated biological specimen that is a smaller opening from the opening for insertion of the biological specimen, and is configured to allow the insertion and removal of the morcellator into the internal cavity and further comprising a retractable sleeve of at least 3 cm in length, made of a thin flexible material, and comprising first and second openings, wherein the first opening of the sleeve encompasses, and is circumferentially coupled to the perimeter, or adjacent to said perimeter, of the opening for removal of the morcellated biological specimen, and further comprising a flexible ring 2 to 6 cm in diameter circumferentially coupled to the perimeter of the second opening of the sleeve and configured such that sleeve can be rolled up around it.

2. The containment system of claim 1, wherein the flexible ring is operably coupled to a pull cord for lengthening the sleeve away from the internal cavity.

3. A method of morcellating a biological specimen within a patient comprising:
  a) providing a containment system used for laparoscopic morcellation comprising a thin, flexible membrane having an outer surface and an inner surface that defines an internal cavity sufficiently large enough to contain a biological specimen targeted for surgical morcellation within a patient, and wherein the containment system further comprises a closable opening on the outer surface of the membrane for insertion of the biological specimen into the internal cavity, and further comprising an opening for removal of the morcellated biological specimen that is a smaller opening from the opening for insertion of the biological specimen, and further comprising a retractable sleeve of at least 3 cm in length, made of a thin flexible material, and comprising first and second openings, wherein the first opening of the sleeve encompasses, and is circumferentially coupled to the perimeter, or adjacent to said perimeter, of the opening for removal of the morcellated biological specimen, and further comprising a flexible ring 2 to 6 cm in diameter circumferentially coupled to the perimeter of the second opening of the sleeve and configured such that sleeve can be rolled up around it;
  b) targeting a biological specimen for morcellation within a surgical cavity of a patient, wherein the surgical cavity comprises an anterior wall;
  c) positioning the biological specimen into the internal cavity of the containment system through the opening for insertion of the biological specimen and subsequently closing said opening for insertion of the biological specimen;
  d) inserting the morcellator into the internal cavity;
  e) morcellating the biological specimen with the morcellator such that no morcellated tissue escapes into the surgical cavity;
  f) removing said morcellator from the internal cavity; and
  g) removing said morcellated tissue through the opening for removal of the morcellated biological specimen.

4. The method of morcellating a biological specimen within a patient of claim 3, wherein the morcellator is inserted into the internal cavity through an opening selected from the group consisting of: the opening for removal of the biological specimen, and the opening for insertion of the biological specimen.

5. The method of claim 3, wherein the morcellator is inserted and removed from the internal cavity through the retractable sleeve and the opening for removal of the biological specimen.

6. The method of claim 5, wherein the morcellator is inserted and removed from the internal cavity through a trocar sleeve that is positioned inside the retractable sleeve and extends into the internal cavity.

7. The method of claim 6, wherein the containment system further comprises a pull string coupled to the flexible ring, and further comprising pulling the pull string such that the coupled flexible ring compresses and is pulled into the morcellator's trocar sleeve, and then removing the morcellator trocar sleeve from within the patient's anterior wall, thereby exteriorizing the retractable sleeve and flexible ring.

8. The method of claim 7, further comprising rolling up the retractable sleeve around the exteriorized flexible ring.

9. The method of claim 8, further comprising reinserting the morcellator trocar sleeve through the rolled up retractable sleeve and the opening for removal of biological specimen and inserting the morcellator through the morcellator trocar sleeve and into the internal cavity of the containment system.

10. The method of claim 3, further comprising rolling up the retractable sleeve around the exteriorized flexible ring.

* * * * *